(12) United States Patent
Liu et al.

(10) Patent No.: US 7,205,900 B2
(45) Date of Patent: Apr. 17, 2007

(54) WATER DETECTING SYSTEM AND RELATED METHOD OF PORTABLE ELECTRIC DEVICE

(75) Inventors: Feng-Chi Liu, Chia-I (TW); Jung-Tsan Weng, Tai-Nan County (TW)

(73) Assignee: BenQ Corporation, Gueishan, Tao-Yuan Hsien (TW)

( * ) Notice: Subject to any disclaimer, the term of this patent is extended or adjusted under 35 U.S.C. 154(b) by 260 days.

(21) Appl. No.: 10/906,866

(22) Filed: Mar. 9, 2005

(65) Prior Publication Data

US 2006/0208914 A1 Sep. 21, 2006

(51) Int. Cl.
*G01R 31/08* (2006.01)
*G08B 210/00* (2006.01)

(52) U.S. Cl. ............... 340/604; 324/522; 73/304 R; 340/605

(58) Field of Classification Search .......... 340/604, 340/539.1–539.28; 324/522–526

See application file for complete search history.

(56) References Cited

U.S. PATENT DOCUMENTS

| | | | |
|---|---|---|---|
| 3,372,246 A | 3/1968 | Knuepfer | |
| 3,525,902 A * | 8/1970 | Prickett et al. | 361/178 |
| 6,363,218 B1 * | 3/2002 | Lowenstein et al. | 392/498 |
| 6,629,021 B2 * | 9/2003 | Cline et al. | 700/300 |
| 7,050,837 B2 * | 5/2006 | Menz et al. | 455/572 |

* cited by examiner

*Primary Examiner*—Daniel Wu
*Assistant Examiner*—Jennifer Mehmood
(74) *Attorney, Agent, or Firm*—Winston Hsu

(57) ABSTRACT

A water detecting system of a portable electric device comprises a housing, an electronic circuitry board, a battery electrically connected to the electronic circuitry board for providing electrical power to the electronic circuitry board, and at least one pair of electric terminals, the pair of electric terminals comprising one positive terminal and one negative terminal located in close proximity to the positive terminal. When the pair of electric terminals are electrically conducted, a current runs through the pair of electric terminals. The water detecting system also comprises a current detector electrically connected to the pair of electric terminals for detecting if the current running through the pair of electric terminals exceeds a threshold level, and a switch connected to the current detector and the battery for disconnecting the battery from the electronic circuitry board when the current exceeds the threshold level.

14 Claims, 3 Drawing Sheets

WATER DETECTING SYSTEM AND RELATED METHOD OF PORTABLE ELECTRIC DEVICE

BACKGROUND OF INVENTION

1. Field of the Invention

The present invention relates to a water detecting system for protecting electronic circuitry of a portable electric device when water enters the portable electric device.

2. Description of the Prior Art

As portable electric devices such as mobile phones, personal digital assistants (PDAs), and notebook computers become a bigger part of people's lives, it also becomes more important to limit the damage caused to these portable electric devices from exposure to water. It is well known that water has the potential to damage electric devices. When the electric devices are operating at the time that they are exposed to water, the damage can be especially severe. Water can short circuit electronic circuitry that is in use, causing irreparable damage to the electronic circuitry.

The traditional defense against water damage is to seal off all openings of the electric device to make the electric device waterproof. Please refer to FIG. 1. FIG. 1 is a cross section diagram of a water proofing system 10 according to the prior art. The water proofing system 10 shown is used for sealing keys 18 of an electric device's keypad for preventing water from entering the electric device through openings in the keypad. Each key 18 is covered with a waterproof boot 12. Each waterproof boot 12 contains a dome section 14 and a foot 16. The dome section 14 is flexible, and can be pressed downward for allowing a user to press the keys 18 of the electric device. Since all openings in the keypad are completely covered by the water proof boots 12, the water proofing system 10 protects the electric device from water damage.

Unfortunately, the water proofing system 10 shown in FIG. 1 is expensive to produce and use of the water proofing system 10 makes it difficult to reduce the size of the electric devices utilizing it. Moreover, if water is able to enter into the electric devices through other openings or cracks in the housing of the electric device that have not been waterproofed, the electronic circuitry of the electric device may still become damaged. That is, the water proofing system 10 provides no protection for the electronic circuitry of the electric device when water permeates through the outer housing of the electric device and does not detect that water has entered the outer housing.

SUMMARY OF INVENTION

It is therefore an objective of the claimed invention to provide a water detecting system that disconnects power supplied to an electronic circuitry board of a portable electric device when detecting the presence of water inside the portable electric device to solve the above-mentioned problems.

According to the claimed invention, a water detecting system of a portable electric device comprises a housing, an electronic circuitry board of the portable electric device disposed inside the housing, a battery electrically connected to the electronic circuitry board for providing electrical power to the electronic circuitry board, and at least one pair of electric terminals, the pair of electric terminals comprising one positive terminal and one negative terminal located in close proximity to the positive terminal, wherein when the pair of electric terminals are electrically conducted, a current runs through the pair of electric terminals. The water detecting system also comprises a current detector electrically connected to the pair of electric terminals for detecting if the current running through the pair of electric terminals exceeds a threshold level, and a switch connected to the current detector and the battery for disconnecting the battery from the electronic circuitry board when the current exceeds the threshold level.

The invention also relates to a method of detecting water entering a portable electric device. The method comprises providing at least one pair of electric terminals, the pair of electric terminals comprising one positive terminal and one negative terminal located in close proximity to the positive terminal, wherein when the pair of electric terminals are electrically conducted, a current runs through the pair of electric terminals. The method also comprises supplying electrical power to an electronic circuitry board of the portable electric device, detecting if the current running through the pair of electric terminals exceeds a threshold level, and disconnecting the supply of electrical power to the electronic circuitry board when the current exceeds the threshold level.

It is an advantage of the claimed invention that the switch disconnects the power supplied by the battery to the electronic circuitry board of the portable electric device if the current detector detects that water has contacted the pair of electric terminals. The electronic circuitry located on the electronic circuitry board will not be short circuited by any water that may reach the electronic circuitry since no power is supplied to the electronic circuitry board. Thus, significant damage to the electronic circuitry of the portable electric device can be avoided.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
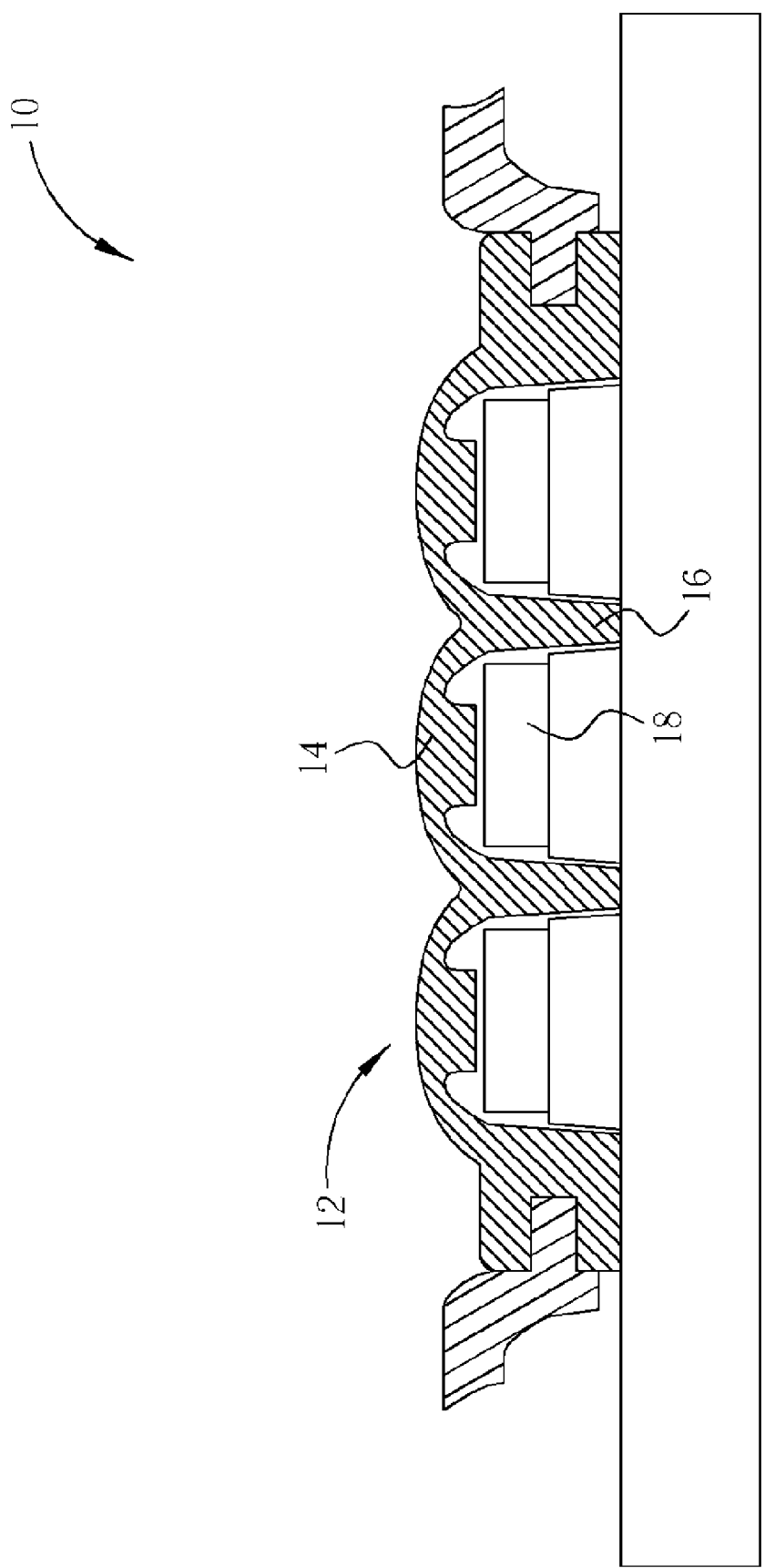
FIG. 1 is a cross section diagram of a water proofing system according to the prior art.
Figure 2:
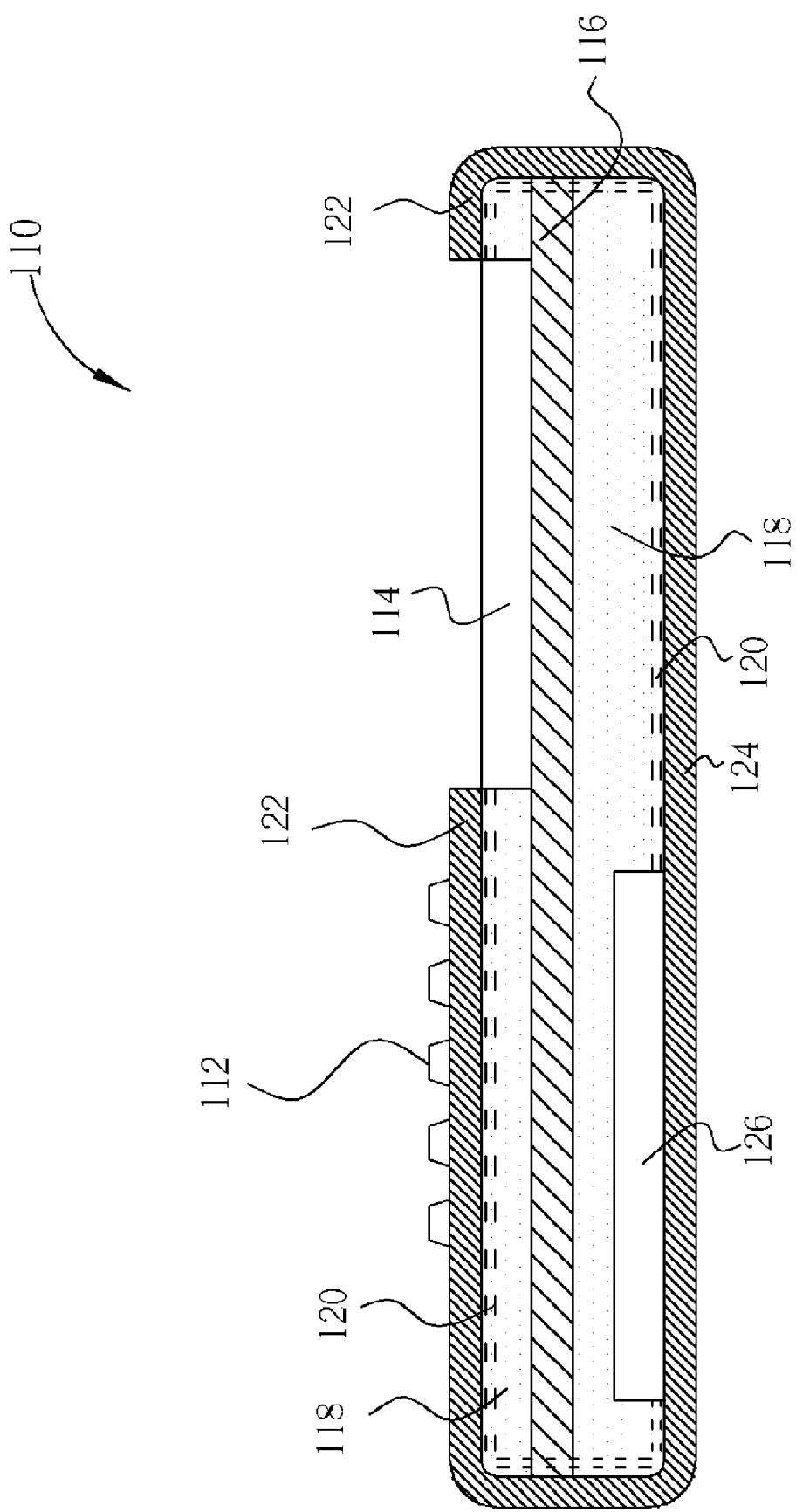
FIG. 2 is a diagram of a portable electric device utilizing a water detecting system according to the present invention.

Please refer to FIG. 2. FIG. 2 is a diagram of a portable electric device 110 utilizing a water detecting system according to the present invention. As an example, the portable electric device 110 shown in FIG. 2 is a mobile phone. However, any portable electric device that has openings through which water may enter the portable electric device can also use the water detecting system of the present invention.

The portable electric device 110 comprises a plurality of keys 112 disposed on a front housing 122 of the portable electric device 110. A display 114, such as an LCD display, is also formed on an upper surface of the portable electric device 110. A rear housing 124 connects with the front housing 122 for forming an outer housing of the portable electric device 110. A circuit board 116, such as a printed circuit board, is disposed between the front housing 122 and the rear housing 124. The circuit board 116 contains electronic circuitry for controlling operation of the portable electric device 110. A battery 126 is used for supplying electrical power to the electronic circuitry located on the circuit board 116.

If water were to enter inside the portable electric device 110, the most likely places for the water to enter would be through openings in the front housing 122 or the rear housing 124 of the portable electric device 110. To help prevent water that enters inside the portable electric device 110 from reaching the electronic circuitry on the circuit board 116, water-absorbing material 118 is placed inside the front housing 122 and the rear housing 124 for absorbing water that enters the portable electric device 110. The water-absorbing material 118 can be a sponge, or any other type of material that can absorb water.

Besides that the water-absorbing material 118 absorbing water that enters the portable electric device 110 to protect the electronic circuitry from being short circuited, it also prevents damage from large amount of water by embedding a plurality of pairs of electric terminals 120 in the water-absorbing material 118. The electric terminals can be in contact with the water-absorbing material 118 as well. It this way, water-absorbing material acts as a good conductor to make the two terminals electrically connected more quickly when the water comes into the water-absorbing material and before the water touches the circuit board. Therefore, the water is detected if the two terminals are electrically connected. More specific description of the electric terminals is included in the following paragraph. However, please note that the water-absorbing material 118 is optional since water itself is a conductor of the terminals, but the water-absorbing material 118 is preferably used for reducing the amount of damage done to the electronic circuitry on the circuit board 116.

Figure 3:
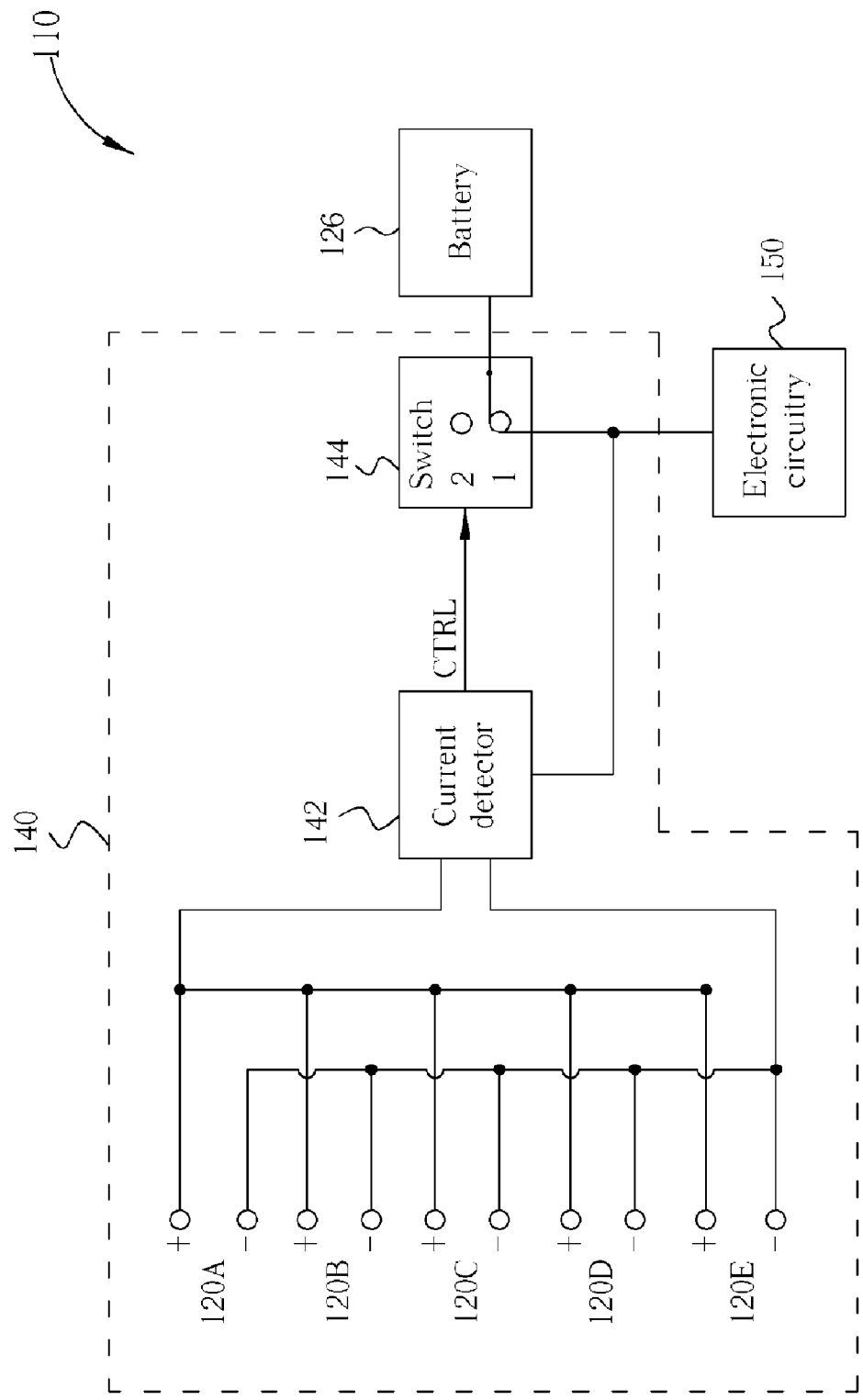
FIG. 3 is a diagram illustrating a water detecting system utilized in the portable electric device according to the present invention.

Please refer to FIG. 3. FIG. 3 is a diagram illustrating a water detecting system 140 utilized in the portable electric device 110 according to the present invention. The water detecting system 140 contains plurality of pairs of electric terminals 120A–120E used for detecting water entering the portable electric device 110. Only five pairs of electric terminals 120A–120E are shown in FIG. 3 for simplicity, and any number of pairs of electric terminals can be used in the present invention. The pairs are placed inside the front housing 122 and the rear housing 124 of the portable electric device 110. The pairs of electric terminals 120 are preferably placed near openings in the front housing 122 and the rear housing 124 for detecting water that enters the portable electric device 110 as soon as possible. Each pair of electric terminals 120 contains a positive terminal and a negative terminal. In normal conditions, the positive terminal and the negative terminal are not electrically connected, and therefore, no current runs through the pair of electric terminals 120. However, if water enters the portable electric device 110, water acts as a conductor that electrically connects the positive terminal to the negative terminal of the pair of electric terminals 120. Therefore, water contacting at least one of the pairs of electric terminals 120 causes electrical current to run through one or more of the pairs of electric terminals 120. The water detecting system 140 also contains a current detector 142 connected to the pairs of electric terminals 120A–120E for detecting current running through one or more of the pairs of electric terminals 120A–120E. The current detector 142 detects whether the current running through the pairs of electric terminals 120A–120E is greater than a threshold value, and controls a switch 144 using a control signal CTRL output from the current detector 142. If the current detected by the current detector 142 is less than or equal to the threshold value, the control signal CTRL controls the switch 144 to move to the first position. When the switch 144 is in the first position, the battery 126 remains to supply electrical power to electronic circuitry 150 of the portable electric device 110 and to the current detector 142. On the other hand, if the current detected by the current detector 142 exceeds the threshold value, the control signal CTRL controls the switch 144 to move to the second position. In the second position, the battery 126 is electrically disconnected from both the current detector 142 and the electronic circuitry 150.

When the portable electric device 110 is operating normally and has not been exposed to water, the switch 144 is set to the first position. However, as soon as water reaches any of the pairs of electric terminals 120A–120E, the current detector 142 controls the switch 144 to change to the second position, for cutting off the supply of electrical power from the battery 126 to the electronic circuitry 150 and the current detector 142. Because no electrical power is supplied to the electronic circuitry 150 of the portable electric device 110, the water cannot short circuit the electronic circuitry 150 of the portable electric device 110, cause the circuits to burn out, or cause other major irreparable damage to the portable electric device 110.

To prevent users from turning the portable electric device 110 back on when the portable electric device 110 is still wet inside, the switch 144 can only be manually changed from the second position back to the first position by a trained technician. Thus, when the portable electric device 110 gets wet and the current detector 142 turns the switch 144 to the second position, users should take the portable electric device 110 into a service center or an authorized dealer to have a technician ensure that the portable electric device 110 is completely dry before moving the switch 144 from the second position back to the first position for restoring the supply of electrical power from the battery 126 back to the electronic circuitry 150 and the current detector 142.

In summary, the water detecting system of the present invention disconnects the power supplied by the battery to the electronic circuitry on the circuit board of the portable electric device when the current detector detects that water has contacted the pair of electric terminals. By doing so, the water detecting system ensures that the electronic circuitry of the portable electric device will not be short circuited by any water that may reach the electronic circuitry. Thus, significant damage to the electronic circuitry of the portable electric device can be avoided. In addition, the user is prevented from resetting the switch to supply power to the electronic circuitry without having a trained technician inspect the portable electric device to make sure that the portable electric device is dry. Because of this, the chance of electrical damage to the electronic circuitry of the portable electric device is greatly reduced.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A water detecting system of a portable electric device, for detecting water entering the portable electric device, comprising:
   a housing;
   an electronic circuitry board of the portable electric device disposed inside the housing;

a battery electrically connected to the electronic circuitry board for providing electrical power to the electronic circuitry board;

at least one pair of electric terminals, the pair of electric terminals comprising one positive terminal and one negative terminal located in close proximity to the positive terminal, wherein when the pair of electric terminals are electrically conducted by contacting the water, a current runs through the pair of electric terminals;

a current detector electrically connected to the pair of electric terminals for detecting if the current running through the pair of electric terminals exceeds a threshold level; and a switch connected to the current detector and the battery for disconnecting the battery from the electronic circuitry board when the current exceeds the threshold level.

2. The water detecting system of claim 1, wherein when water contacts the pair of electric terminals, the positive terminal electrically connects to the negative terminal, thereby inducing the current to run through the pair of electric terminals.

3. The water detecting system of claim 1, further comprising water-absorbing material disposed inside of the housing for absorbing water entering through openings in the housing.

4. The water detecting system of claim 3, wherein the water-absorbing material is a sponge.

5. The water detecting system of claim 3, further comprising a plurality of pairs of electric terminals contact with the water-absorbing material, wherein the current detector detects if the current running through any of the pairs of electric terminals exceeds the threshold level.

6. The water detecting system of claim 1, further comprising a plurality of pairs of electric terminals, wherein the current detector detects if the current running through any of the pairs of electric terminals exceeds the threshold level.

7. The water detecting system of claim 6, wherein the pairs of electric terminals are disposed inside of the housing near openings in the housing.

8. A method of detecting water entering a portable electric device, for detecting water entering the portable electric device, the method comprising:

providing at least one pair of electric terminals, the pair of electric terminals comprising one positive terminal and one negative terminal located in close proximity to the positive terminal, wherein when the pair of electric terminals are electrically conducted by contacting the water, a current runs through the pair of electric terminals;

supplying electrical power to an electronic circuitry board of the portable electric device;

detecting if the current running through the pair of electric terminals exceeds a threshold level; and disconnecting the supply of electrical power to the electronic circuitry board when the current exceeds the threshold level.

9. The method of claim 8, wherein when water contacts the pair of electric terminals, the positive terminal electrically connects to the negative terminal, thereby inducing an electric current to run through the pair of electric terminals.

10. The method of claim 8, further comprising disposing water-absorbing material inside of the portable electric device for absorbing water entering the portable electric device.

11. The method of claim 10, wherein the water-absorbing material is a sponge.

12. The method of claim 10, wherein a plurality of pairs of electric terminals are disposed in the water-absorbing material, and the method comprises detecting when the current running through any of the pairs of electric terminals exceeds the threshold level.

13. The method of claim 8, further comprising providing a plurality of pairs of electric terminals, and the method comprises detecting when the current running through any of the pairs of electric terminals exceeds the threshold level.

14. The method of claim 13, wherein the plurality of pairs of electric terminals are disposed inside a housing of the portable electric device near openings in the housing.

* * * * *